(12) United States Patent
Spassov et al.

(10) Patent No.: US 7,107,156 B2
(45) Date of Patent: Sep. 12, 2006

(54) METHOD AND APPARATUS FOR ESTIMATING SOLVATION ENERGIES OF MEMBRANE BOUND MOLECULES

(75) Inventors: Velin Zlatkov Spassov, San Diego, CA (US); Liqun Yan, San Diego, CA (US); Sandor Szalma, San Diego, CA (US)

(73) Assignee: Accelrys Software Inc., San Diego, CA (US)

( * ) Notice: Subject to any disclaimer, the term of this patent is extended or adjusted under 35 U.S.C. 154(b) by 281 days.

(21) Appl. No.: 10/205,594

(22) Filed: Jul. 23, 2002

(65) Prior Publication Data

US 2003/0033129 A1    Feb. 13, 2003

Related U.S. Application Data

(60) Provisional application No. 60/307,502, filed on Jul. 23, 2001.

(51) Int. Cl.
G06F 19/00 (2006.01)
G01N 33/48 (2006.01)
G01N 31/00 (2006.01)
G06G 7/48 (2006.01)

(52) U.S. Cl. ............................ 702/27; 702/19; 702/22; 703/11

(58) Field of Classification Search ................ 702/19, 702/22, 20; 703/11
See application file for complete search history.

(56) References Cited

U.S. PATENT DOCUMENTS 5,420,805 A * 5/1995 Still et al. ................... 703/6
6,226,603 B1 * 5/2001 Freire et al. ................. 703/11

OTHER PUBLICATIONS

Arbuzova et al. "Membrane Binding of Peptides Containing Both Basic and Aromatic Residues. Experimental Studies with Peptides Corresponding to the Scaffolding Region of Caveolin and the Effector Region of MARKS" Biochemisty 2000, 39, 10330-10339.*
Im et al. (1998) Continuum solvation model: computation of electrostatic forces from numerical solutions to the Poisson-Boltzmann equation. *Computer Physics Communications.* 111:59-75.
White et al. (1999) Membrane protein folding and stability: physical principles. *Annu. Rev. Biophys. Biomol. Struct.* 28:319-65.
Bursulaya et al. (2000) Comparative study of the folding free energy landscape of a three-stranded β-sheet protein with explicit and implicit solvent models. *J. Phys. Chem. B*. 104:12378-12383.
Hawkins et al. (1996) Parametrized models of aqueous free energies of solvation based on pairwise descreening of solute atomic charges from a dielectric medium. *J. Phys. Chem.* 100:19824-19839.
Onufriev et al. (2000) Modification of the generalized born model suitable for macromolecules. *J. Phys. Chem. B*. 104:3712-3720.
Schaefer et al. (1998) A comprehensive analytical treatment of continuum electrostatics. *J. Phys. Chem.* 100:1578-1579.
Still et al. (1990) Semianalytical treatment of solvation for molecular mechanics and dynamics. *J. Am. Chem. Soc.* 112:6127-6129.

Qiu et al. (1997) The GB/SA continuum model for solvation. A fast analytical method for the calculation of approximate born radii. *J. Phys. Chem. A*. 101:3005-3014.
Scarsi et al. (1997) Continuum electrostatic energies of macromolecules in aqueous solutions. *J. Phys. Chem.* 101:8098-8106.
Dominy et al. (1999) Development of a generalized born model parametrization for proteins and nucleic acids. *J. Phys. Chem. B*. 103:3765-3773.
Bashford et al. (2000) Generalized born models of macromolecules solvation effects. *Annu. Rev. Phys. Chem.* 51:129-52.
Luecke et al. (1999) Structure of bacteriorhodopsin at 1.55 Å resolution. *J. Mol. Biol.* 291:899-911.
Macosko et al. (1997) The membrane topology of the fusion peptide region of influenza hemagglutinin determined by spin-labeling EPR. *J. Mol. Biol.* 267:1139-1148.
Palczewski et al. (2000) Crystal structure of rhodopsin: a G protein-coupled receptor. *Science.* 289:739-745.
Karshikoff et al. (1994) Electrostatic properties of two porin channels from *Escherichia coli*. *J. Mol. Biol.* 240:372-384.
Bechor et al. (2001) Implicit solvent model studies of the interactions of the influenza hemagglutinin fusion peptide with lipid bilayers. *Biophysical Journal.* 80:643-655.
Zhou et al. (2000) $^{15}$N NMR study of the ionization properties of the influenza virus fusion peptide In zwitterionic phospholipid dispersions. *Biophysical Journal.* 78:2418-2425.
Wesson et al. (1992) Atomic solvation parameters applied to molecular dynamics of proteins in solution. *Protein Science.* 1:227-235. Cambridge University Press.
Parsegian (1969) Energy of an ion crossing a low dielectric membrane: solutions to four relevant electrostatic problems. *Nature.* 221:844-846.
Bashford et al. (1992) Electrostatic calculations of the $pK_a$ values of ionizable groups in bacteriorhodopsin. *J. Mol. Biol.* 224:473-486.
Lee et al. (1971) The interpretation of protein structures: estimation of static accessibility. *J. Mol. Biol.* 55:379-400.
Schaefer et al. (1999) Solution conformations of structured peptides: continuum electrostatics versus distance-dependent dielectric functions. *Theor Chem Acc.* 101:194-204.
Bashford (1997) An object-oriented programming suite for electrostatic effects in biological molecules—An experience report on the MEAD project. *Scientific Computing in Object-Oriented Parallel Environments.* pp. 233-240.

* cited by examiner

*Primary Examiner*—John S. Brusca
*Assistant Examiner*—Eric S. DeJong
(74) *Attorney, Agent, or Firm*—Knobbe Martens Olson & Bear LLP (57) ABSTRACT

The disclosure relates to a method of estimating the polar component of the solvation energy for a molecule embedded in different media. In one embodiment, the molecule is partially embedded in a membrane. For an atom of the molecule, the polar component of the atom's solvation energy is represented as a combination of at least a self-energy term and a screening-effect term. The self-energy term represents the contribution to the atom's polar component made by the membrane and the molecule's other atoms located inside the membrane. The screening-effect term represents the typically negative contribution to the atom's polar component made by the molecule's other atoms located outside the membrane. An analytical function is used to calculate the self-energy term.

31 Claims, 8 Drawing Sheets

METHOD AND APPARATUS FOR ESTIMATING SOLVATION ENERGIES OF MEMBRANE BOUND MOLECULES

CROSS REFERENCE TO RELATED APPLICATIONS

This application claims priority under 35 U.S.C. §119(e) to U.S. Provisional Patent Application No. 60/307,502, titled "METHOD OF ESTIMATING SOLVATION ENERGIES OF MEMBRANE BOUND MOLECULES" and filed Jul. 23, 2001. The above-referenced Provisional Patent Application is hereby incorporated by reference in its entirety.

BACKGROUND OF THE INVENTION

1. Field of the Invention

This invention relates to the field of molecular modeling and more particularly to the field of calculating solvation energy.

2. Description to the Related Art

In the computational analysis of molecules, inter-atomic forces are modeled to determine the configurations of individual molecules, multi-molecular entities, and the tendencies of separate molecules to form bound complexes. Because these configuration and affinities are highly dependent on the interaction between the modeled molecules and the surrounding solvent molecules (typically water), a variety of models have been devised to account for the molecule-solvent interactions.

One such method involves explicitly including the individual solvent molecules in the area around the molecules of interest. However, this is very expensive computationally, because thousands of solvent-related atomic positions and inter-atomic forces must often be computed, in addition to those involving the molecules of interest themselves. Accordingly, many attempts have been made to simplify this analysis, and to compute a free energy of solvation for a given configuration of molecule or multi-molecular entity, based on principles of electrostatics that treat the solvent as a dielectric continuum in which the molecules of interest are embedded.

The following formula represents one commonly used model of calculating the solvation energy of a molecule:

$$G_{sol} = G_{pol} + G_{np} \quad (Eq.1)$$

In the above formula, $G_{sol}$ represents the solvation energy of the molecule, $G_{pol}$ represents the polarization component of the solvation energy (polar solvation energy), and $G_{np}$ represents the non-polar component of the solvation energy (non-polar solvation energy). The non-polar component $G_{np}$ can be estimated using the following formula:

$$G_{np} = \sigma SA \quad (Eq.2)$$

In the above formula, SA is the total solvent accessible area of the molecule, and $\sigma$ is an empirical parameter. The above equation can be modified to a summation over individual atoms of the molecule, as shown in the following equation:

$$G_{np} = \Sigma_i \sigma_i SA_i \quad (Eq.3)$$

The polar solvation energy $G_{pol}$ can be calculated by methods such as the Poisson-Boltzman (PB) method, the generalized Born (GB) method, the analytical continuum electrostatic potential (ACE) method, and so forth.

In the generalized Born method, the polar solvation energy is determined using the following equation:

$$G_{pol} = -166(1/\epsilon_m - 1/\epsilon_w)\Sigma_i\Sigma_j q_i q_j / (r_{ij}^2 + a_i a_j \exp(-r_{ij}^2/4a_i a_j))^{0.5}. \quad (Eq.4)$$

In the above formula, $\epsilon_m$ is a dielectric constant of the molecule, $\epsilon_w$ is a dielectric parameter of the solvent, $q_i$ is the partial charge of the atom i, $q_j$ is the partial charge of the atom j, $a_i$ and $a_j$ are known as the respective effective Born radii of the atoms i and j, and $r_{ij}$ is the distance between atoms i and j. In the above formula, the summations are taken over all atoms of the molecule. If the effective Born radius of every atom is established, then the molecule's polar solvation energy can be calculated.

The effective Born radius of a given atom in a molecule may be generally characterized as the van der Waals radius of the atom increased by an amount characterizing the degree to which the atom is screened from interacting with the solvent by the other atoms of the molecule. More screening equates to a larger effective Born radius. A larger effective Born radius equates to a smaller contribution to the molecule's polar solvation energy computed with Eq.4.

The effective Born radius of an atom i is typically calculated by setting the charge on the atom $q_i$ to 1, and approximating the polar component of the solvation energy of the atom $G_{pol,i}$ of the molecule using a number of numerical methods, or an analytical solution when possible. Once the polar solvation energy for the an atom is estimated, the effective Born radius is calculated as follows:

$$a_i = -166(1/\epsilon_m - 1/\epsilon_w)/G_{pol,i}. \quad (Eq.5)$$

Many practical methods of calculating $a_i$ and $G_{pol,i}$ use a Coulomb Field approximation:

$$a_i^{-1} = 1/4\pi \int_{ex} r^{-4} dV = R_i^{-1} - 1/(4\pi) \int_{in, r>Ri} r^{-4} dV \quad (Eq.6)$$

$$G_{pol,i} = -(1/\epsilon_m - 1/\epsilon_w)166/4\pi \int_{ex} r^{-4} dV = -(1/\epsilon_m - 1/\epsilon_w) 166(R_i^{-1} - 1/4\pi \int_{in, r>Ri} r^{-4} dV) \quad (Eq.7)$$

The first term $-(1/\epsilon_m - 1/\epsilon_w)166 R_i^{-1}$ may be termed the "self energy" of the solvated atom if regarded as a single ion having one unit positive charge. The term $\int_{in, r>Ri} r^{-4} dV$ in the above equations Eq.6 and Eq.7 is an integration over the region inside the molecule but outside the van der Waals radius of atom i, which evaluates the screening effect of the rest of the molecule. More details of the above equation are provided in Bashford & Case, Ann. Rev. Phys. Chem., 51, 129–152 (2000), which is incorporated herein by reference in its entirety.

According to a method introduced by Still, the polar component $G_{pol,i}$ for atom i is calculated using the following discrete sum over the atoms of the molecule rather than a volume integral:

$$G_{pol,i} = -166(1/\epsilon_m - 1/\epsilon_w)[1/(P_0 + R_i) - \Sigma P V_j / r_{ij}^4]. \quad (Eq.8)$$

In the above equation, $R_i$ is the van der Waals radius of atom i, $V_j$ is the volume of atom j defined by its van der Waals radius, and $P_0$ and $P$ are empirically determined parameters. As shown in the above equations, the polar solvation energy contribution of an atom i is related to its position relative to other atoms j of the molecule.

The determined polar component $G_{pol,i}$ is used in Eq.6 to determine the effective Born radius for the atom i.

The determined effective Born radii for the atoms are then used in Eq.4 to determine the polar solvation energy of the molecule. With the polar solvation energy determined, the solvation energy can be determined using Eq.1. More details of the generalized Born method and the Still method are provided in U.S. Pat. No. 5,420,805 and Still et al., J. Am.

Chem. Soc., 112, 6127–6129 (1990), both of which are hereby incorporated by reference in their entireties.

A variety of modifications and improvements to the original Still formula have been developed which also involve sums over the atoms of the molecule. For example, the following linear pair-wise approximation equation can also be used to derive a polar component of the solvation energy of an atom in a molecule:

$$G_{pol,i} = -(1/\epsilon_m - 1/\epsilon_w)[166/(\lambda R_{vdw,i}) + 166 * P_1/(R^2_{vdw,i}) + \Sigma_{bond,j} P_2 V_j/r_{ij}^4 + \Sigma_{angle,j} P_3 V_j/r_{ij}^4 + \Sigma_{nonbond,j} P_4 V_j/r_{ij}^4 C(r_{ij}, R_{vdw,i}, R_{vdw,j}, P_5)]. \quad (Eq.9)$$

In the above equation, $\lambda$, $P_1$, $P_2$, $P_3$, $P_4$, and $P_5$ represent empirical parameters. $R_{vdw,i}$ and $R_{vdw,j}$ represent the van der Waals radii of atoms i and j. The summation terms are used in Eq.9 to approximate the polar component of an atom i. In Eq.9, the other atoms j are separated into three types: atoms that form direct bonds with atom i (represented by the $\Sigma_{bond,j}$ term), atoms that form indirect bonds with atom i (represented by the $\Sigma_{angle,j}$ term), and atoms that do not form bonds with atom i (represented by the $\Sigma_{nonbond,j}$ term). $C(r_{ij}, R_{vdw,i}, R_{vdw,j}, P_5)$ represents an analytical function that is at least a function of $r_{ij}$, $R_{vdw,i}$ $R_{vdw,j}$, and $P_5$. The other atoms j include all atoms of the molecule that contribute to the polar component of the atom i. In one embodiment for ease of formulation, the other atoms j include all atoms of the molecule. More details of the above equation are provided in Dominy & Brooks, J. Phys. Chem. B, 103, 3765–3773 (1999), incorporated herein by reference in its entirety.

Another pair-wise approximation equation similar to Eq.9 can also be used:

$$G_{pol,i} = -(1/\epsilon_m - 1/\epsilon_w)[166/(R_{vdw,i} + \phi + P_1) + \Sigma_{bond,j} P_2 V_j/r_{ij}^4 + \Sigma_{angle,j} P_3 V_j/r_{ij}^4 + \Sigma_{nonbond,j} P_4 V_j/r_{ij}^4 C(r_{ij}, R_{vdw,i}, R_{vdw,j}, P_5)]. \quad (Eq.10)$$

In the above equation, $\phi$, $P_1$, $P_2$, $P_3$, $P_4$, and $P_5$ represent empirical parameters. $C(r_{ij}, R_{vdw,i}, R_{vdw,j}, P_5)$ represents an analytical function that is at least a function of $r_{ij}$, $R_{vdw,i}$, $R_{vdw,j}$, and $P_5$. More details of the above equation are provided in Qui et al., J. Phys. Chem. B., 101, 3005–3014 (1997), also incorporated herein by reference in its entirety. As described above with respect to the integral formulations, the first term or terms of these equations which do not involve sums over the atoms of the system can be considered the "self energy" terms, and the sums are the "screening effect" terms.

Compared to explicitly including solvent molecules in the simulation, the generalized Born method requires fewer calculations, while producing results similar to those obtained by a more computationally intensive method, such as by using the Poisson-Boltzmann equation. Therefore, the generalized Born method facilitates dynamic simulation with long trajectories for large molecule systems, such as globular proteins and DNA.

However, the existing generalized Born method assumes that the solvent is homogeneous in all directions surrounding the molecular system being modeled. It has thus not been applied to study solvation effects in non-homogeneous media, or in environments having regions outside the solute molecule(s) which have different dielectric constants. As mentioned above, one example of such a system with biological and clinical significance are proteins which are partially embedded in cell membrane and partially in aqueous solution. Trans-membrane proteins are important drug targets, but since trans-membrane proteins are typically partially embedded in a hydrophobic lipid bilayer of cell membrane and partially embedded in a polar aqueous solution, the generalized Born methods described above have not been suitable for modeling trans-membrane proteins. Furthermore, since methods of crystallizing trans-membrane proteins are under-developed, and the results from solid state NMR measurements are still sparse, little is known about the structure of these proteins in native form and the mechanism of their actions. The limited number of 3-D structures limits the use of the homology modeling method for predicting trans-membrane protein structures.

Although other computational methods such as the Poisson-Boltzmann equation can be used to calculate the solvation energy of a molecule in a more complex solvent system, the computational complexity is significant.

SUMMARY OF THE INVENTION

In one embodiment, the invention comprises a method of modeling a molecular system comprising a plurality of atoms in an environment having a first region characterized by a first dielectric constant and a second region characterized by a second dielectric constant. The method may comprise estimating a contribution to the polar energy of solvation for an atom using a function which is dependent on the position of the atom with respect to the first region, and which is independent of the position of the atom with respect to other atoms of the plurality of atoms. The estimated contribution may be combined with another contribution to the polar solvation energy which is dependent on the position of the atom with respect to other atoms of the plurality of atoms; and the combined value is used in a Generalized Born equation to estimate the solvation energy of the molecular system.

In another embodiment, the invention comprises a method of estimating a polar component of a solvation energy of a molecule, the molecule being embedded in a first medium and a second medium, the first medium forming a substantially regular geometric shape. In this embodiment, the method comprises for each atom of the molecule, using an analytical function to estimate a first term of contribution to a polar component of a solvation energy of the atom made by the first medium and other atoms of the molecule that are located in the first medium, and determining a second term of contribution to the polar component of the solvation energy of the atom made by others atoms of the molecule that are located at least partially outside the first medium. The first term and the second term are combined to determine the polar component of the solvation energy of the atom. The determined polar components of solvation energies of all atoms of the molecule are used to determine the polar component of the solvation energy of the molecule.

In another embodiment a method of computing configuration energies of molecules or molecular systems is provided. In this embodiment, the molecules or molecular systems being modeled are in an environment including at least a first region characterized by a first dielectric constant and a second region characterized by a second dielectric constant. The configuration energies are computed at least in part by computing atomic solvation energies of atoms in the molecules or molecular systems. The method comprises modeling at least a portion of the atomic solvation energy of an atom as an analytical function which depends on the position of the atom with respect to one of the regions, and which does not depend on the position of any other atoms of the molecule.

Systems for modeling molecules or molecular systems which are configured or programmed to implement the methods disclosed herein are also provided.

DETAILED DESCRIPTION OF THE PREFERRED EMBODIMENT

Embodiments of the invention will now be described with reference to the accompanying Figures, wherein like numerals refer to like elements throughout. The terminology used in the description presented herein is not intended to be interpreted in any limited or restrictive manner, simply because it is being utilized in conjunction with a detailed description of certain specific embodiments of the invention. Furthermore, embodiments of the invention may include several novel features, no single one of which is solely responsible for its desirable attributes or which is essential to practicing the inventions herein described.

Since trans-membrane proteins, for example G-protein coupled receptors, are important drug targets, it is desirable to develop methods of estimating electrostatic energy terms in membrane-bound molecules. It is also desirable to develop methods that can compute fairly quickly and produce fairly accurate estimates. It is further desirable to develop general methods of estimating the solvation energy and its polar component for a molecule embedded in different media. In addition, it is desirable to develop a method, whose computational complexity of calculating the solvation energy of a molecule in two different media is not significantly higher than calculating the solvation energy of the molecule in a single medium.

Figure 1:
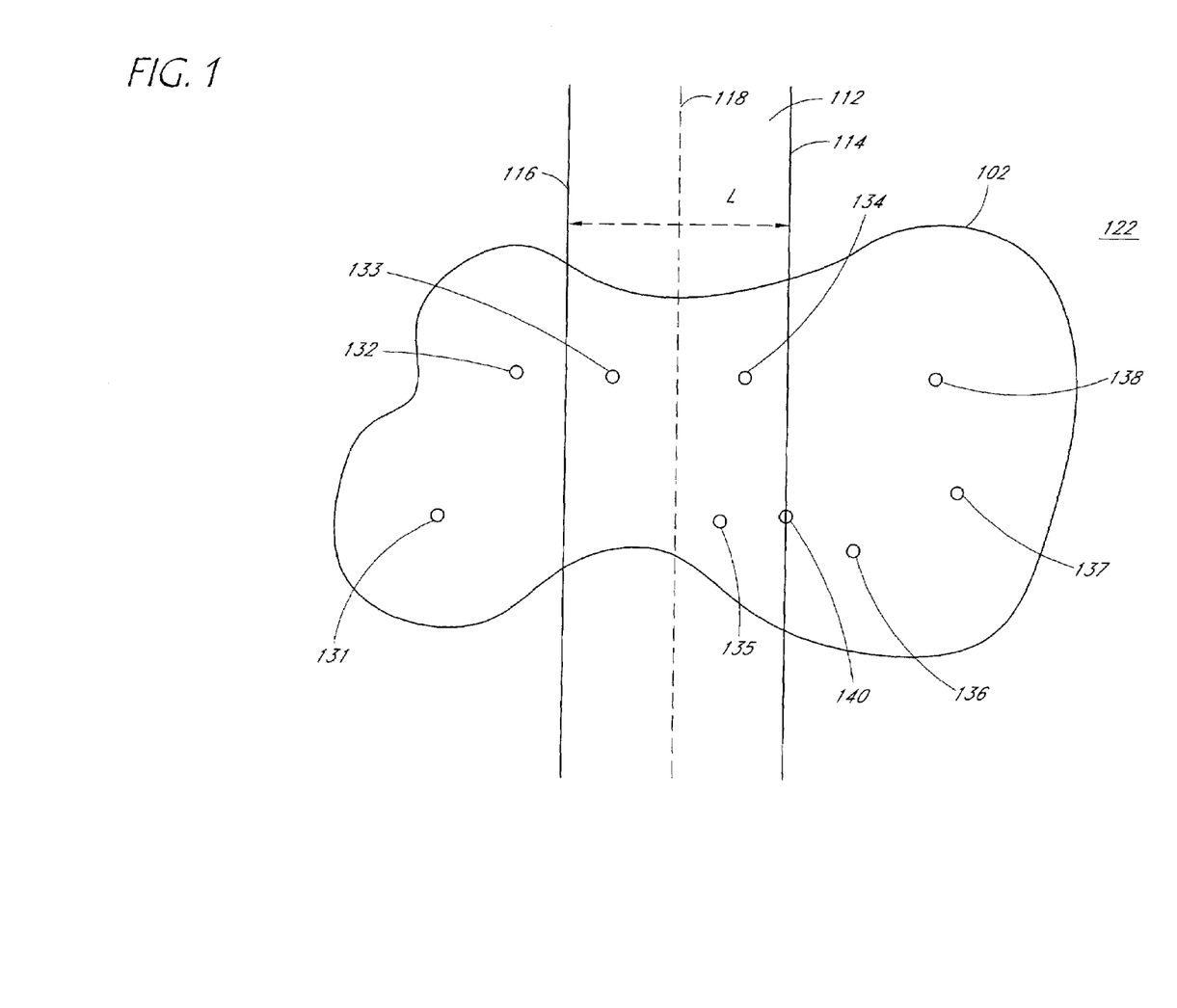
FIG. 1 illustrates one embodiment of a membrane-bound molecule.

FIG. 1 is an illustration of a membrane-bound molecule. This is one particular example of a molecule or molecular system that is embedded in or is near both a first medium and a second medium with different dielectric properties. As shown in FIG. 1, the molecule 102 is partially embedded in a membrane 112. The molecule 102 is also partially embedded in aqueous solution 122. The membrane slab 112 includes lipid bilayers of border 114 and border 116, and a midplane 118. The midplane 118 is the line parallel to the borders 114 and 116, and of equal distance to the borders 114 and 116. The thickness of the membrane is the distance L from border 114 to border 116.

The molecule 112 includes a plurality of atoms. The atoms 131–138 and 140 are shown in FIG. 1 for ease of illustration. In reality, a molecule 112 may include hundreds or thousands of atoms. The atoms 133, 134, and 135 are inside the membrane 112. The atoms 131, 132, 136, 137, and 138 are outside the membrane 112. The atom 140 is partially inside the membrane 112 and partially outside the membrane 112.

Figure 2:
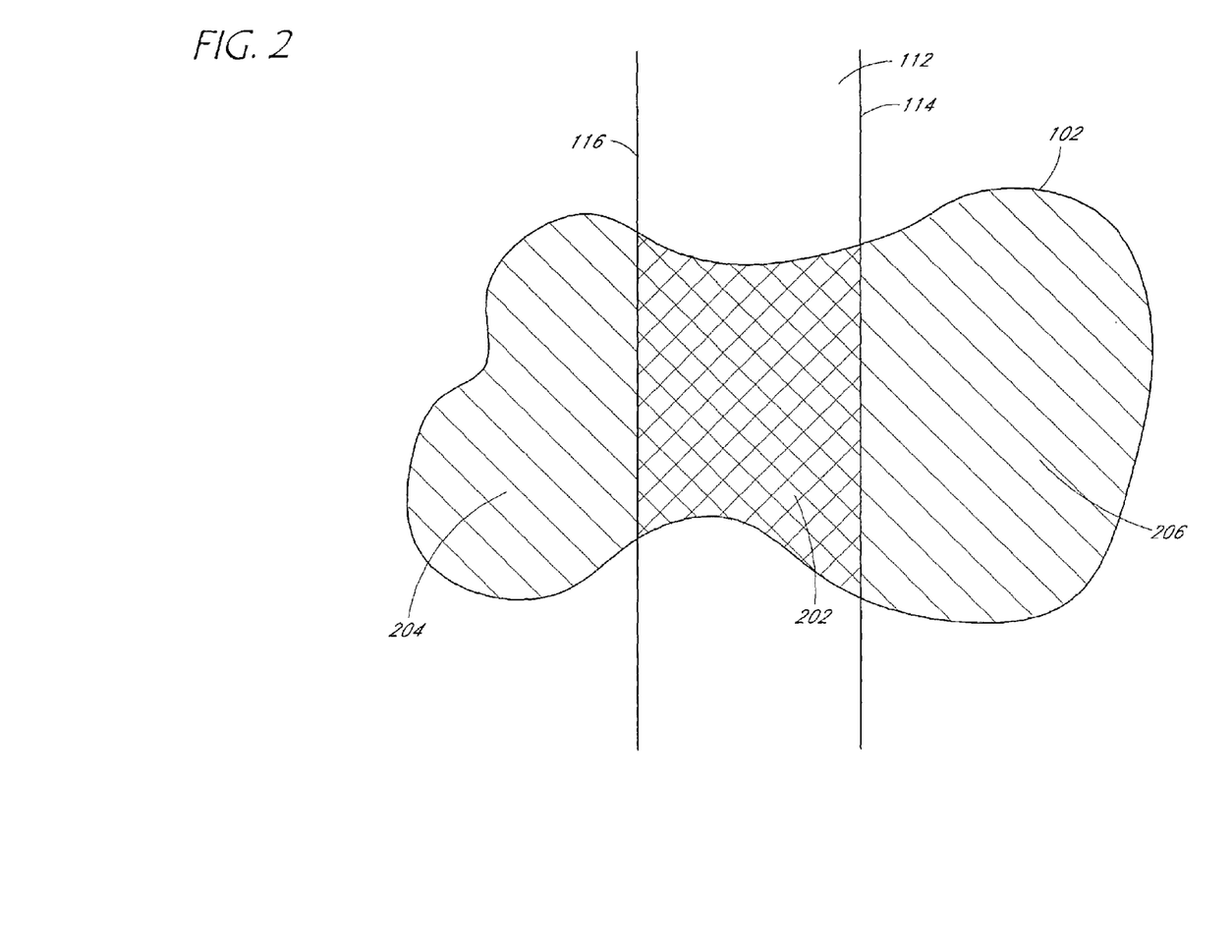
FIG. 2 illustrates multiple areas of a membrane-bound molecule.

FIG. 2 illustrates multiple areas of the membrane-bound molecule which is illustrated in FIG. 1. As shown in FIG. 2, the molecule 102 is partially embedded in membrane 112. The membrane 112 bilayers divide the molecule 102 into an area 202 inside the membrane 112, and areas 204 and 206 outside the membrane 112.

As described above, for an atom i of the molecule 102, its solvation energy polar component $G_{pol,i}$ may be characterized as including a self-energy contribution plus a screening-effect contribution. In conventional Generalized Born models of molecules embedded in a single homogeneous dielectric media, the self energy contribution is the solvation energy of the charged atom without considering the other atoms of the molecule. The inventors have found that the Generalized Born method can be extended to systems having multiple regions of different dielectric media if a portion of what would normally be considered the screening effect contribution is combined with the conventional self energy contribution. When combined in the appropriate way, the conventional self energy expression plus this portion of the screening contribution can be substituted with a relatively simple and easily calculable analytical expression that produces accurate results with little computational expense.

Turning back to the membrane example of FIG. 2, the conventional self energy expression described above may be combined with the screening effect from the planar slab which includes the membrane 112 and the portion of the molecule 102 within the membrane. This produces what may be termed a "composite self energy" expression that is modeled with a simple analytical formula. In one embodiment, the analytical function is a function of a distance between the atom and the membrane central plane, the van der Waals radius of the atom, and the thickness of the membrane 112.

In formulating this approach, it is assumed that the dielectric constant inside the protein is equal to the dielectric constant of the membrane itself. This is likely a good assumption because the low dielectric constant (~2) inside the hydrophobic part of lipid membranes is consistent with a similar value (~2) inside the protein if most electrostatic interactions, but not the induced polarization are treated explicitly. As will be described below in connection with FIG. 5, this and other approximations have produced promising results.

If, as explained above, it is assumed that the dielectric constant of the protein region within the membrane is equal to the dielectric constant of the membrane itself, the expression for $G_{pol,i}$ of Equation 7 above can be re-written with two separate integrals as follows:

$$G_{pol,i} = -(1/\epsilon_m - 1/\epsilon_w) 166 [R_i^{-1} - 1/(4\pi) \int_{in,r>Ri} r^{-4} dV - 1/(4\pi) \int_{out,r>Ri} r^{-4} dV] \quad (\text{Eq.11})$$

In the above equation Eq.11, $\int_{in,r>Ri} r^{-4} dV$ represents an integration over the membrane slab 112, and $\int_{out,r>Ri} r^{-4} dV$ represents an integration over the region of the molecule outside the membrane slab 112.

It has been recognized by the inventors that the first two terms of Equation 11 are the self energy of an ion (e.g. atom i with charge set to 1 as described above) in the presence of only the membrane and surrounding aqueous solvent. Because of the symmetry of this solvent system, which may be modeled as an infinite slab of dielectric constant $\epsilon_m$, embedded in water of dielectric constant $\epsilon_w$, this self energy can be computed fairly easily using the Poisson-Boltzmann method, and will depend on the distance $Z_i$ between the atom with respect to the center of the membrane.

Based on Poisson-Boltzmann computations, the inventors have further found that this self energy can be advantageously modeled with an analytical function $\Gamma(Z_i, R_i, L)$ that can be used to replace the term $(R_1^{-1} - 1/(4\pi) \int_{in, r>Ri} r^{-4} dV)$ in Eq.13, which results in the following equation for $G_{pol,i}$:

$$G_{pol,i} = -(1/\epsilon_m - 1/\epsilon_w) 166 (\Gamma - 1/(4\pi) \int_{out, r>Ri} r^{-4} dV) \quad \text{(Eq.12)}$$

It will be appreciated that the alternative discrete sum formulations for $G_{pol,i}$ can also be modified by replacing their self energy terms with an analytical function $\Gamma$ such as the equation set forth below:

$$G_{pol,i} = -(1/\epsilon_m - 1/\epsilon_w)[\Gamma + \Sigma_{bond,j,out} P_2 V_j / R_{ij}^4 + \Sigma_{angle,j,out} P_3 V_j / R_{ij}^4 + \Sigma_{nonbond,j,out} P_4 V_j / R_{ij}^4 C(r_{ij}, R_{vdw,j}, P_5)]. \quad \text{(Eq.13)}$$

One embodiment of the analytical function $\Gamma$ is a sigmoid type function including an empirical parameter $\gamma$:

$$\Gamma(Z_i, R_{vdw,i}, L) = g_i^{slv} + (g^{cntr}(L) - g_i^{slv}) / \{1 + \exp[\gamma(|z_i| + R_{vdw,i} - L/2)]\}. \quad \text{(Eq.14)}$$

This sigmoid type function has been found to fit polar solvation self energies calculated using Poisson-Boltzman. In the above equation, $z_i$ is the distance from the atom to the membrane midplane, and L is the thickness of the membrane. In one embodiment, the term $g^{cntr}$ of the above equation is the self energy of a centrally located ion. This value has been calculated, and can be determined by the following equation:

$$g^{cntr} = -332 \ln(2)/L. \quad \text{(Eq.15)}$$

More details of the above equation are provided in Parsegian, Nature, 221, 844–846 (1969). The term $g_i^{slv}$ in Eq.20 is the self energy at an infinite distance from the membrane, and may be set to $166/R_i$, which is the usual value for a solvated ion in water.

In the above equation, the summation terms $\Sigma_{bond,j,out}$, $\Sigma_{angle,j,out}$, and $\Sigma_{nonbond,j,out}$ are taken over the molecule's atoms that are located outside the membrane slab 112, such as atoms 131, 132, 136–138. Atom 140, which is partially within, and partially outside the membrane can be considered in a variety of ways. In one embodiment, atom 140 is considered in the membrane if its center is in the membrane, and outside the membrane if its center is outside the membrane. In another embodiment, the term $V_j$ represents the volume of the atom j which is located outside the membrane 112. In this embodiment, $V_j$ will depend on Z.

In some embodiments, therefore, a function $V_j(Z_i)$ can be used to replace $V_j$, resulting in the following equation:

$$G_{pol,i} = -(1/\epsilon_m - 1/\epsilon_w)[\Gamma + \Sigma_{bond,j,out} P_2 V_j(Z_j)/R_{ij}^4 + \Sigma_{angle,j,out} P_3 V_j(Z_j)/R_{ij}^4 + \Sigma_{nonbond,j,out} P_4 V_j(Z_j)/R_{ij}^4 C(r_{ij}, R_{vdw,i}, P_5)]. \quad \text{(Eq.16)}$$

The term $V_j(Z_j)$, representing a volume of the atom j outside the membrane, is expressed as a function of the distance from the atom j to the membrane. The term is used to include the contribution of an atom j located partially inside the membrane and partially outside the membrane. In one embodiment, $V_j(Z_j)$ can be determined by the following equation:

$$V_j(Z_j) = \pi h^2 (R_{vdw,j} - h/3). \quad \text{(Eq.17)}$$

The above function is used as a smoothing function to include in the screening-effect term the contribution of an atom located partially outside the membrane slab 112, such as atom 140 of FIG. 1. If the atom is located completely inside the membrane 112, where z is less than (L/2)−R, h is defined as 0. If the atom is completely outside the membrane 112, where z is greater than (L/2)+R, h is defined as the van de Waals radius of the atom. If the atom is partially inside and partially outside the membrane 112, where z is between (L/2)−R and (L/2)+R, h is defined as z+R−(L/2). With this formula, the atomic volume used in the sums is the atomic volume which extends beyond the membrane outer surface.

Figure 3:
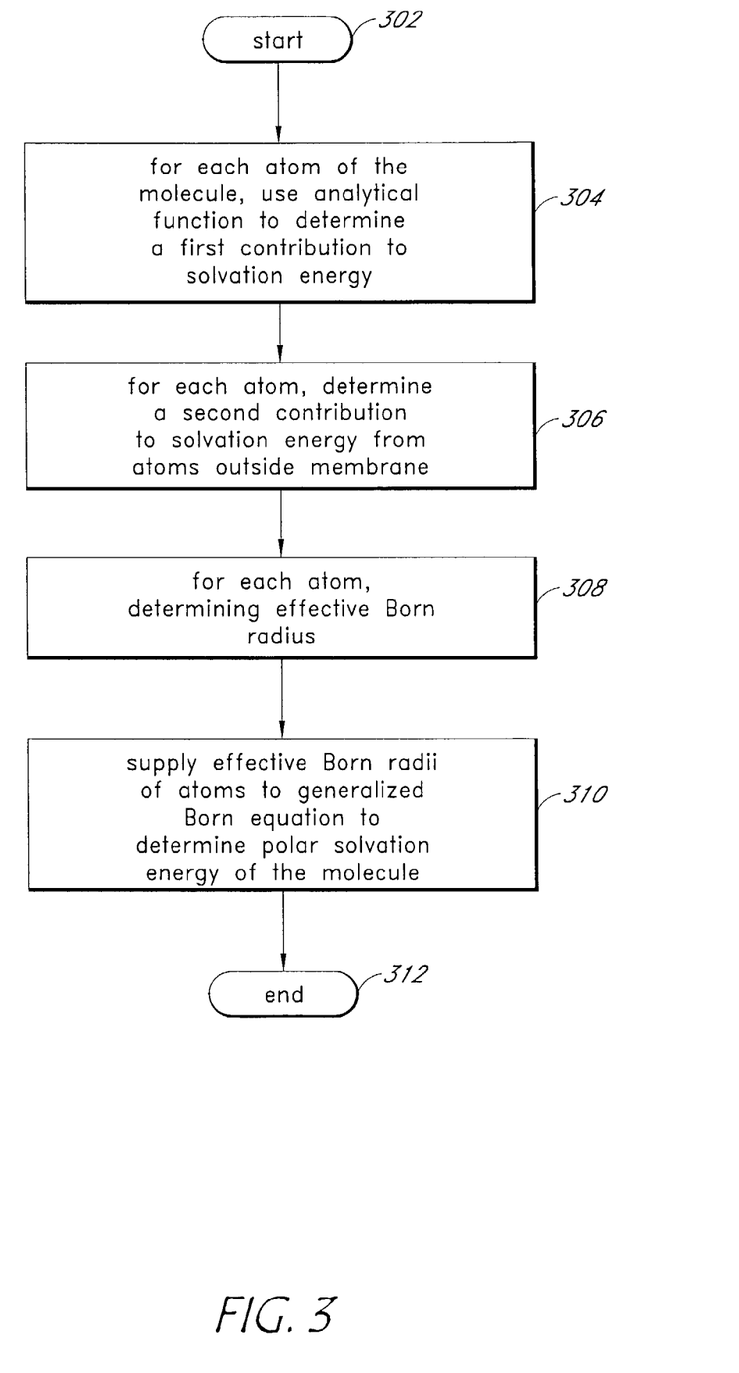
FIG. 3 illustrates one embodiment of a process of estimating polar component of a membrane-bound molecule.

FIG. 3 illustrates one embodiment of a process of estimating the polar solvation energy of a membrane-bound molecule. The process begins from a start block 302 and proceeds to a block 304. At block 304, for each atom of the membrane-bound molecule, an analytical function with one or more empirical parameters is used to determine the a contribution to the atom's polar solvation energy. In other words, the analytical function is used to determine the self-energy component of the atom's solvation energy. In one embodiment, Eq.20 is used to determine the analytical function $\Gamma$.

Although the parameters such as $\gamma$ may be pre-selected, in some embodiments, prior to block 304, the process determines the one or more empirical parameters used by the analytical function. The empirical parameters can be determined by fitting the predictions of the analytical formula to the results of accurate Poisson-Boltzmann calculations by adjusting the parameter or parameters of the formula. Thus, in one embodiment, the process determines a parameter $\gamma$, which will be used in Eq.20 to define a specific analytical function $\Gamma$. More details on determining empirical parameters will be described below in connection with FIG. 5 and FIG. 6.

Referring back to FIG. 3, the process proceeds from block 304 to block 306. At block 306, for each atom of the membrane-bound molecule, the process determines the screening-effect made by the molecule's atoms located outside the membrane. In one embodiment, the summation terms $\Sigma_{bond,j,out}$, $\Sigma_{angle,j,out}$, $\Sigma_{nonbond,j,out}$, as shown in Eq.17, or the summation terms $\Sigma_{bond,j,out}$, $\Sigma_{angle,j,out}$, $\Sigma_{nonbond,j,out}$, as shown in Eq.18, can be used to determine the screening-effect term. In another embodiment, the term $1/(166*4\pi) \int_{out, r>Ri} r^{-4} dV)$, as shown in Eq.16, can also be used to determine the screening-effect.

The atom's solvation energy polar component is determined by combining the atom's self-energy term, as determined in block 304, with the atom's screening-effect term(s), as determined in block 306. The process proceeds from block 306 to block 308, where each atom's effective Born radius is determined. In one embodiment, since the atom's polar solvation energy has been determined, the atom's effective Born radius is determined using Eq.6. The process proceeds from block 308 to block 310. At block 310, the determined effective Born radius of each atom is used, for example in the generalized Born equation of Eq.4, to determine the polar solvation energy of the molecule. The process proceeds from block 310 to an end block 312.

Figure 4:
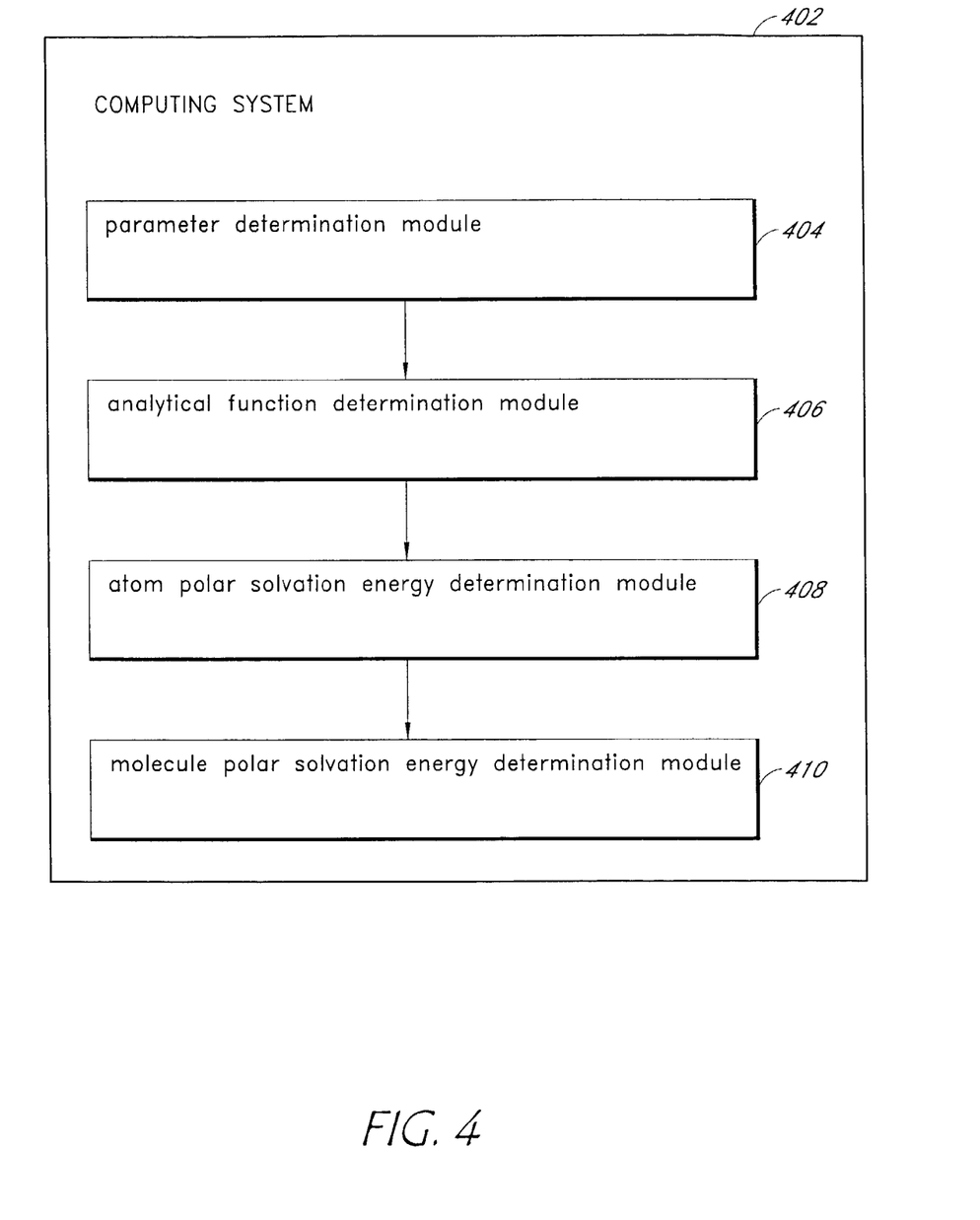
FIG. 4 illustrates one embodiment of a computing system for determining the polar component of a membrane-bound molecule.

FIG. 4 illustrates one embodiment of a computing system for determining the polar solvation energy of a membrane-bound molecule. Referring to FIG. 4, the system 402 may include a parameter determination module 404, an analytical function determination module 406, an atom polar component determination module 408, and a molecule polar solvation energy determination module 410. As used herein, the word "module" refers not only to logic coded as a collection of software instructions, but also to logic embodied in hardware or firmware.

The parameter determination module 404, when present, determines empirical parameters, which are used by the analytical function determination module 406. The parameter determination module 404 receives as input the polar components of atoms of experimental molecules. The received polar components have been determined using other methods, such as the Poisson-Boltzman method. The parameter determination module 404 generates the empirical parameters of the analytical function to produce a desired fit to Poisson-Boltzmann calculations, for example. More details of determining empirical parameters are described below in connection with FIG. 5 and FIG. 6. In one embodiment, the parameter determination module 404 determines the value of the parameter γ as used in Eq.14.

The analytical function determination module 406 receives the determined empirical parameters from the parameter determination module 404, and calculates a self-energy term of an atom's solvation energy polar component, based on the analytical function. In one embodiment, Eq.14 is used to determine the atom's self-energy term.

The atom polar component determination module 408 receives the analytical function value determined by the analytical function determination module 406, and calculates the polar solvation energy of an atom.

The molecule polar solvation energy determination module 410 receives the value of each atom's polar component from the atom polar component determination module 408. The molecule polar solvation energy determination module 410 then determines the polar solvation energy of the molecule. In one embodiment, the molecule polar solvation energy determination module 410 determines each molecule atom's effective Born radius based on the atom's polar component, using Eq.6. In another embodiment, the analytical function determination module 406 or the atom polar component determination module 408 directly calculates the effective Born radius of an atom. The module 410 then determines the molecule's polar solvation energy. In one embodiment, the module 410 uses the determined effective Born radii of the atoms and Eq.4 to determine the molecule's polar solvation energy.

In one embodiment, parameter determination is performed by another system, therefore the parameter determination module 404 is omitted from the computing system 402. As those skilled in the art will appreciate, a module can be separated into multiple modules, and multiple modules can be combined into fewer modules, to perform the same functions. In each of these cases, combinations of modules are included within the definition of "module."

Once the molecule's polar solvation energy is determined, it can be used to determine the total solvation energy of the molecule, using Eq.1. In the case of membrane bound molecular systems, the non-polar component of the total solvation energy is also an important consideration. It has been found that when modeling globular non-membrane bound proteins in aqueous solution, the non-polar component of the solvation energy is much less significant than the polar component, and that the low energy conformation is not very sensitive to this part of the solvation energy. However, for membrane bound proteins, this component of the solvation energy is a significant force attracting the protein to the membrane interior. Therefore, the σSA term becomes more important to accurately estimate. In some embodiments of the invention, a value for σ of 28 cal/Å² has been used with good results, wherein the solvent accessible surface area is computed with respect to the atoms outside the membrane only.

The molecule's estimated solvation energy in selected conformations and over the course of a dynamic simulation can be used to predict the physical properties of drug-candidate molecules, and to select drug-candidate molecules for further studying or synthesizing. The method and system described in the present application can be used to study the electrostatic effects of macromolecules, trans-membrane proteins, and other molecules located in two different media.

In addition to membrane containing systems, the described method and system can be used to study the electrostatic effect of polymer absorption. The described method and system are particularly suitable when the discrete dielectric regions are a substantially regular geometric shape, for example a plane formed by a membrane, a substantially circular region formed by an oil droplet, a substantially spherical or cylindrical shell region formed by spherical or cylindrical micelles, and the like. When the solvent system has appropriate symmetries, self energies can be calculated and fitted to a simple function of atomic position. In some cases, the functional form may be derivable from electrostatic theory.

Figure 5:
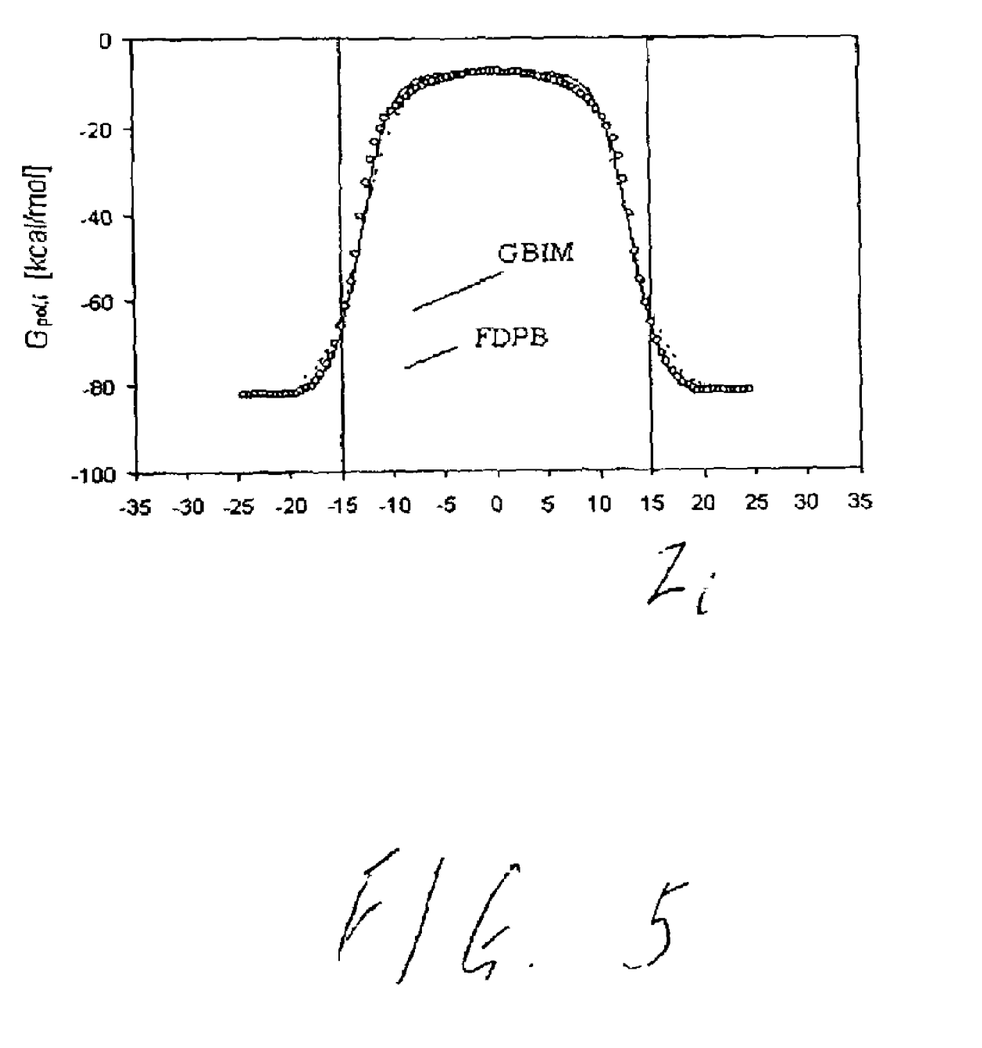
FIG. 5 illustrates one embodiment of polar components of atoms over distance, calculated by different methods.

FIG. 5 illustrates a graph of solvation self energy of an ion as a function of distance $z_i$ from the atom to the membrane midplane, calculated by different methods. A spherical ion of radius of 2 angstroms and one unit of electric charge was used for these calculations. A membrane with a thickness of 30A and a dielectric parameter of 1 is also used in this model. The polar component of the ion is calculated using Finite-Difference solvers of the Poisson-Boltzman equation (FDPB). In FIG. 5, the circles represent values obtained by the FDPB method. The solid line represents values obtained by the above described the analytical function, using a value of γ=0.71. The dotted line represents values obtained by the above described analytical function, using a value of γ=0.55. Calculations have indicated that the results obtained using the FDPB method and the sigmoid function match especially well when the membrane slab is not very thin, for example, when the thickness L is greater than 20A.

Figure 6:
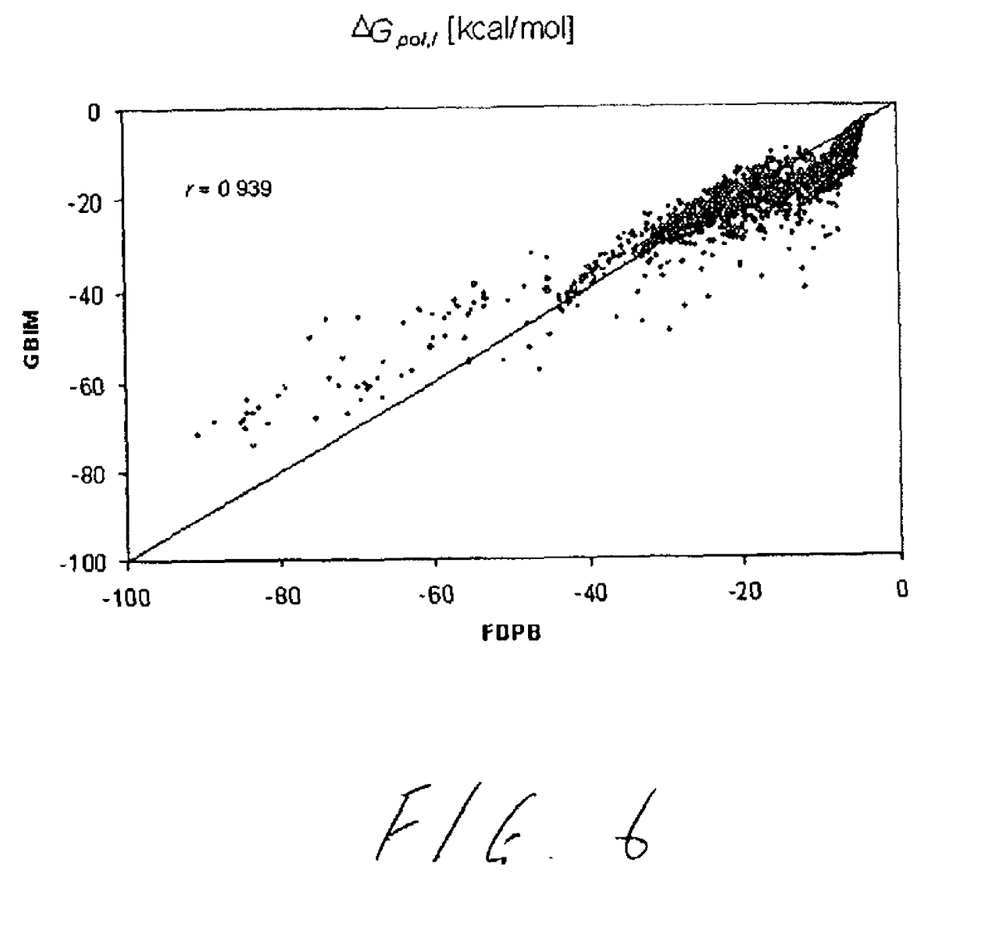
FIG. 6 illustrates one embodiment of polar components of atoms over distance, calculated by different methods.

FIG. 6 illustrates one embodiment of polar components of atoms over distance, calculated by different methods. The data in FIG. 6 are obtained from a modeled bacteriorhodopsin structure with 2087 atoms centered in a 30A membrane with a dielectric parameter of 2. The extended Generalized Born method described above and the FDPB method were both used to determine the polar solvation energy of each of the atoms. Each atom is plotted in FIG. 6, along with the line of unit slope. A best fit (in terms of maximum r value) is found with a value of γ=0.55.

Depending on the molecules and solvents used in the parameter determination process, other values of γ may also be used. For example, in one embodiment with a single 1 angstrom ion in a 30A membrane with dielectric parameter of 1, a value of γ=0.92 was found to achieve a good fit with FDPB values. Therefore, a plurality of γ parameters may be used in the above-described analytical function. For example, Eq.14 may be modified to the following equation:

$$\Gamma(Z_i, R_{vdw,i}, L) = g_i^{slv} + (g^{cntr}(L) - g_i^{slv})/\{1 + \exp[\gamma_i(z_i + R_{vdw,i} - L/2)]\}. \quad \text{(Eq.22)}$$

In the above equation, $\gamma_i$ is related to the atom i. For example, one value of $\gamma_i$ may be used for atoms with small radii, and another value of $\gamma_i$ may be used for atoms with larger radii. The parameter $\gamma_i$ can be a function of the atom radius. However, increasing the number of γ parameters increases the computational complexity. A number of tests have found that a single γ parameter value has achieved reasonably good fits with FDPB values.

Figure 7:
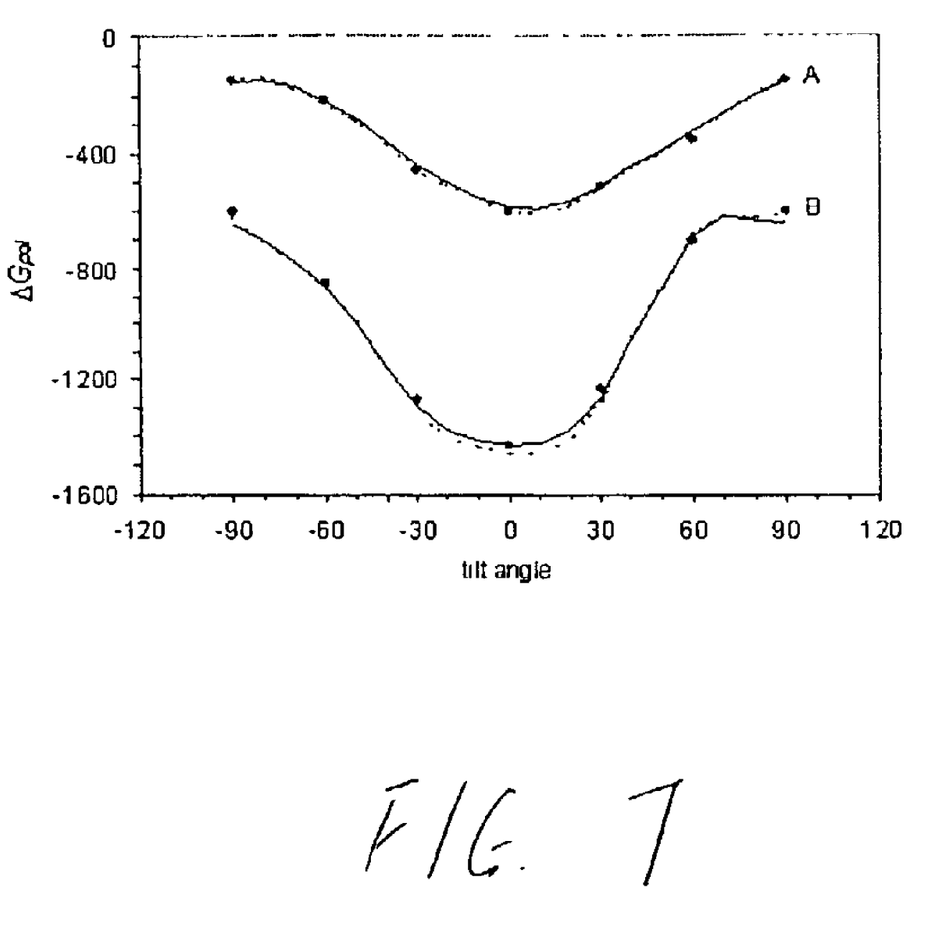
FIG. 7 illustrates one embodiment of the solvation energy values of a molecule at different tile angles with the membrane, calculated by different methods.

FIG. 7 illustrates one embodiment of the solvation energy values molecule at different tilt angles with the membrane, calculated by different methods. The circles represent values produced by the FDPB method. The solid lines represent values produced by the above described method with γ=0.55. The dotted lines represent values produced by the above described Generalized Born method with γ=0.72. Curve A represents the values for bacteriorhodopsin. Curve B represents the values for rhodopsin. The tilt angle is the angle between membrane normal and the molecular principal axis of inertia. As shown in FIG. 7, values produced by the Generalized Born method match reasonably well with values produced by the FDPB method.

Figure 8:
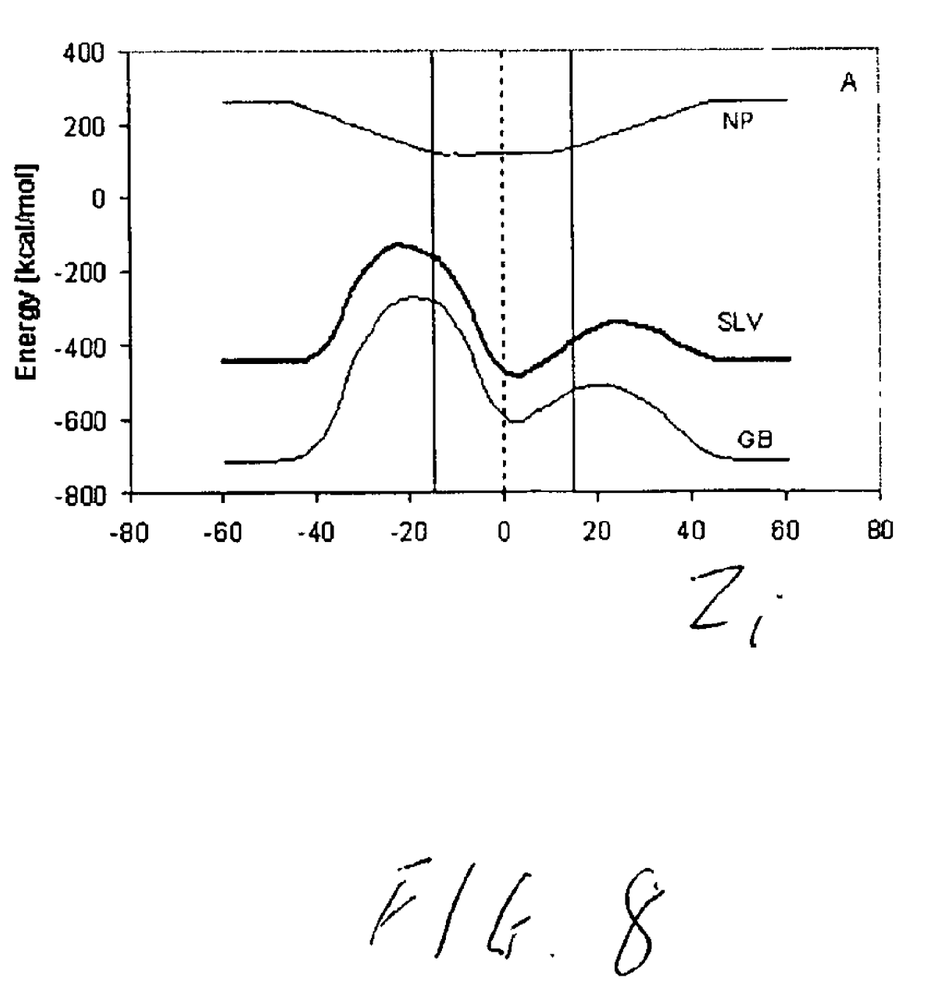
FIG. 8 illustrates one embodiment of the energy values of a molecule at different distances from the membrane.

FIG. 8 illustrates a plot of energy values for a membrane bound bacteriorhodopsin molecule at different distances between the center of mass of the protein and the central plane of the membrane. The X-axis represents the distance from the molecule to the membrane. In one embodiment, the X-axis represents the distance from the center of the mass of the molecule to the center of the membrane. The curve "POL" represents the polar component of the solvation energy of the molecule, calculated by the above-described generalized Born method using an analytical function. The curve "NP" represents the non-polar component of the solvation energy of the molecule. The curve "SLV" represents the total solvation energy of the molecule, as a sum of the polar component and the non-polar component of the solvation energy.

As shown in FIG. 8, the solvation energy of the molecule is asymmetric with respect to position in the membrane. The energy barrier is significantly higher when the molecule crosses the membrane towards the extracellular space than towards the cytoplasmic space. This corresponds with the experimental observation that the cytoplasmic portion of a bacteriorhodopsin is less embedded in the hydrophobic bilayer than the extracellular portion. It seems to be related to the energy penalty for cytoplasmic polar cap to sink into membrane space, which is higher than the energy penalty for a extracellular portion. A similar asymmetric property was observed for rhodopsin.

The foregoing description details certain embodiments of the invention. It will be appreciated, however, that no matter how detailed the foregoing appears in text, the invention can be practiced in many ways. As is also stated above, it should be noted that the use of particular terminology when describing certain features or aspects of the invention should not be taken to imply that the terminology is being re-defined herein to be restricted to including any specific characteristics of the features or aspects of the invention with which that terminology is associated. The scope of the invention should therefore be construed in accordance with the appended claims and any equivalents thereof.

What is claimed is:

1. A method of estimating a polar component of a solvation energy of a molecule, the molecule being partially embedded in a membrane and partially embedded in a solution, the method comprising:
   for each atom of the molecule, using an analytical function of atomic position relative to the midplane of said membrane in a region of the membrane where the molecule is embedded in the membrane to estimate a first contribution to a polar component of a solvation energy of the atom made by the atom itself, by the membrane and the other atoms of the molecule that are located inside the membrane;
   for each atom of the molecule, determining a second contribution to the polar component of the solvation energy of the atom made by other atoms of the molecule that are located at least partially outside the membrane; and
   for each atom of the molecule, combining the first and second contributions to determine the polar component of the solvation energy of the atom; and
   using the atomic polar solvation energies of all atoms of the molecule to determine at least in part the polar solvation energy of the molecule; and displaying one or more results of said polar solvation energy determination.

2. The method of claim 1, wherein for an atom of the molecule, the analytical function is a function of at least a distance between the atom and the membrane center.

3. The method of claim 1, wherein for an atom of the molecule, the analytical function is a function of at least a van der Waals radius of the atom.

4. The method of claim 1, wherein for an atom of the molecule, the analytical function is a function of at least a thickness of the membrane.

5. The method of claim 1, wherein for an atom of the molecule, the analytical function is a function of at least a distance between the atom and the membrane, a van der Waals radius of the atom, and a thickness of the membrane.

6. The method of claim 1, wherein the analytical function includes an empirical parameter, wherein the method further comprises determining a value of the empirical parameter.

7. The method of claim 1, wherein determining a second contribution comprises determining a first summation term of atoms that covalently bond to the atom, a second summation term of atoms that bond to the atom through one intervening atom, and a third summation term of atoms that do not bond to the atom either covalently or through one intervening atom.

8. The method of claim 1, wherein determining a second contribution comprises estimating an integral over a region inside the molecule and outside the van der Waals radius of the atom, for other atoms of the molecule located outside the membrane.

9. The method of claim 1, wherein using the polar solvation energy comprises:
   for each atom of the molecule, determining the atom's effective Born radius based on the atom's polar solvation energy; and
   determining the polar solvation energy of the molecule based on the effective Born radii of all atoms of the molecule.

10. The method of claim 1, wherein using the atomic polar solvation energy comprises:
   for each atom of the molecule, determining the atom's effective Born radius based on the atom's polar solvation energy; and
   determining the polar component of the solvation energy of the molecule with a generalized Born equation.

11. The method of claim 1, wherein the molecule is a macromolecule.

12. A system for calculating a polar component of a solvation energy of a molecule, the molecule being partially embedded in a membrane and partially embedded in a solution, the system comprising:
   an analytical function determination module configured to determine, for each atom of the molecule that contributes to the polar component of the solvation energy of the molecule, a composite self-energy term of contribution to a polar component of a solvation energy of the atom made by the solution, the membrane, and other atoms of the molecule located at least partially inside the membrane, using an analytical function of atomic position relative to the midplane of said membrane in a region of the membrane where the molecule is embedded in the membrane including an empirical parameter;

an atom polar component determination module configured to determine, for each atom of the molecule that contributes to the polar component of the solvation energy of the molecule, the polar component of the solvation energy of the atom, based on the composite self-energy term of the atom and a screening-effect term of the atom, the screening-effect term of the atom being a contribution to the polar component of the solvation energy of the atom made by other atoms of the molecule located at least partially outside the membrane; and a molecule polar solvation energy determination module configured to determine the polar component of the solvation energy of the molecule, based on the determined polar components of the solvation energies of all atoms of the molecule that contribute to the polar component of the solvation energy of the molecule; and an output for communicating results of the polar solvation energy determination module.

13. The system of claim 12, further comprising a parameter determination module configured to determine a value of the empirical parameter.

14. The system of claim 13, wherein the parameter determination module determines a value of the empirical parameter by fitting polar components of solvation energies produced by a Poisson-Boltzmann method against the analytical function.

15. The system of claim 12, wherein the analytical function is a function of at least a distance between the atom and the central plane of the membrane, a van der Waals radius of the atom, and a thickness of the membrane.

16. The system of claim 12, wherein the screening-effect term of an atom comprises a first summation term of atoms that covalently bond with the atom, a second summation term of atoms that bond with the atom through one intervening atom, and a third summation term of atoms that do not bond with the atom either covalently or through one intervening atom.

17. The system of claim 12, wherein the screening-effect term of an atom comprises an estimated integration of a region inside the molecule and outside the van der Waals radius of the atom, for other atoms of the molecule located at least partially outside the membrane.

18. The method of claim 12, wherein the molecule polar component determination module is configured to:

for each atom of the molecule that contribute to the polar component of the solvation energy of the molecule, determining the atom's effective Born radius based on the polar component of the solvation energy of the atom; and determining the molecule's polar solvation energy based on the effective Born radii of all atoms of the molecule that contribute to the polar component of the solvation energy of the molecule.

19. The system of claim 12, further comprising a molecule solvation energy determination module configured to determine the solvation energy of the molecule, based on the determined polar component of the solvation energy of the molecule and a determined non-polar component of the solvation energy of the molecule.

20. A method of estimating a polar component of a solvation energy of a molecule, the molecule being embedded in a first dielectric medium and a second dielectric medium having a different dielectric constant than the first dielectric medium, the first dielectric medium forming a substantially regular geometric shape, the method comprising:

for each atom of the molecule, using an analytical function of atomic position relative to a location in the first dielectric medium to estimate a first term of contribution to a polar component of a solvation energy of the atom made by the first dielectric medium and other atoms of the molecule that are located in the first dielectric medium;

for each atom of the molecule, determining a second term of contribution to the polar component of the solvation energy of the atom made by others atoms of the molecule that are located at least partially outside the first dielectric medium;

for each atom of the molecule, combining the first term and the second term to determine the polar component of the solvation energy of the atom; and using the determined polar components of solvation energies of all atoms of the molecule to determine the polar component of the solvation energy of the molecule; and displaying one or more results of said polar solvation energy determination.

21. The method of claim 20, wherein for an atom of the molecule, the analytical function is a function of at least a position of the atom with respect to the first dielectric medium.

22. The method of claim 20, wherein using the polar components comprises:

for each atom of the molecule, determining the atom's effective Born radius based on the polar component of the solvation energy of the atom; and determining the polar component of the solvation energy of the molecule based on the effective Born radii of all atoms of the molecule.

23. The method of claim 20, wherein the first dielectric medium is a membrane.

24. The method of claim 20, wherein the first dielectric medium is a region of polymer.

25. The method of claim 20, wherein for each atom of the molecule, using an analytical function to estimate a first term comprises using an analytical function including an empirical parameter, wherein a value of the empirical parameter is dependent on a characteristic of the atom.

26. The method of claim 25, wherein a value of the empirical parameter is dependent on a radius of the atom.

27. A method of estimating a polar component of a solvation energy of a molecule, the molecule being embedded in a first dielectric medium and a second dielectric medium having a different dielectric constant than the first dielectric medium, the first dielectric medium forming a substantially regular geometric shape, the method comprising:

for each atom of the molecule, using an analytical function of atomic position relative to a location in the first dielectric medium to estimate a first term of contribution to a polar component of a solvation energy of the atom made by the first dielectric medium and other atoms of the molecule that are located in the first dielectric medium;

for each atom of the molecule, determining a second term of contribution to the polar component of the solvation energy of the atom made by other atoms of the molecule that are located at least partially outside the first dielectric medium;

for each atom of the molecule, using the first term and the second term to determine an effective Born radius of the atom; and using the determined effective Born radii of all atoms of the molecule to determine the polar component of the solvation energy of the molecule; and displaying one or more results of said polar solvation energy determination.

28. The method of claim 27, wherein for an atom of the molecule, the analytical function is a function of at least a position of the atom with respect to the first dielectric medium.

29. The method of claim 28, wherein a distance between the atom and the first dielectric medium is a distance between the atom and the center of the first dielectric medium.

30. The method of claim 27, wherein using the determined effective Born radii comprises using a generalized Born equation to determine the polar component of the solvation energy of the molecule.

31. The method of claim 27, wherein the first dielectric medium forms a planar structure.

* * * * *

UNITED STATES PATENT AND TRADEMARK OFFICE
CERTIFICATE OF CORRECTION

PATENT NO. : 7,107,156 B2
APPLICATION NO. : 10/205594
DATED : September 12, 2006
INVENTOR(S) : Velin Zlatk Spassov et al.

It is certified that error appears in the above-identified patent and that said Letters Patent is hereby corrected as shown below:

First Page, column 1, line 4, under Other Publications which reads "Biochemisty", should read -- Biochemistry --

First Page, column 1, line 19, under Other Publications which reads "(1998)", should read -- (1996) --

First Page, column 2, line 5, under Other Publications after "Chem." please insert -- A. --

First Page, column 2, line 7, under Other Publications which reads "parametrization", should read -- parameterization --

First Page, column 2, line 9, under Other Publications which reads "macromolecules", should read -- macromolecular --

First Page, column 2, line 38, under Other Publications after "Chem" please insert -- . --

Column 1, line 22, which reads "to", should read -- of --

Column 1, line 27, which reads "configuration", should read -- configurations --

Column 2, line 28, which reads "the an", should read -- the --

Column 2, line 31, which reads "a;" should read -- $a_i$ --

Column 3 (Eq. 10), line 32 (approx.), which reads "$(R_{vdw,I}+$", should read -- $(R_{vdw,i}+$ --

Column 7, line 6, which reads "$(R_1^{-1}$" should read -- $(R_i^{-1}$ --

Column 7 (Eq. 16), line 51 (approx.), which reads "$_{nonbond,j,out}$", should read --$\Sigma_{nonbond,j,out}$ --

Column 8, line 4, which reads "z+R-(L/2).", should read -- z +R-(L/2). --

Column 8, line 12, which reads "the a", should read -- the --

Column 8, line 39, after "dV", which reads ")", should read -- , --

UNITED STATES PATENT AND TRADEMARK OFFICE
CERTIFICATE OF CORRECTION

PATENT NO. : 7,107,156 B2
APPLICATION NO. : 10/205594
DATED : September 12, 2006
INVENTOR(S) : Velin Zlatk Spassov et al.

It is certified that error appears in the above-identified patent and that said Letters Patent is hereby corrected as shown below:

Column 10, line 60, which reads "increases", should read -- increase --

Column 11, line 34, which reads "a", should read -- an --

Signed and Sealed this

Fifteenth Day of April, 2008

JON W. DUDAS
*Director of the United States Patent and Trademark Office*